US012698257B2

(12) United States Patent
An et al.

(10) Patent No.: US 12,698,257 B2
(45) Date of Patent: Aug. 4, 2026

(54) METHOD OF PREPARING ACRYLONITRILE DIMER

(71) Applicant: LG CHEM, LTD., Seoul (KR)

(72) Inventors: Yujin An, Daejeon (KR); Wonseok Kim, Daejeon (KR); Hyunchul Jung, Daejeon (KR); Sae Hume Park, Daejeon (KR); Wan Kyu Oh, Daejeon (KR)

(73) Assignee: LG CHEM, LTD., Seoul (KR)

( * ) Notice: Subject to any disclaimer, the term of this patent is extended or adjusted under 35 U.S.C. 154(b) by 972 days.

(21) Appl. No.: 17/634,881

(22) PCT Filed: Jun. 9, 2021

(86) PCT No.: PCT/KR2021/007222
§ 371 (c)(1),
(2) Date: Feb. 11, 2022

(87) PCT Pub. No.: WO2022/080621
PCT Pub. Date: Apr. 21, 2022

(65) Prior Publication Data
US 2022/0356149 A1    Nov. 10, 2022

(30) Foreign Application Priority Data

Oct. 12, 2020    (KR) ........................ 10-2020-0131026

(51) Int. Cl.
| | |
|---|---|
| *C07C 255/09* | (2006.01) |
| *B01J 27/228* | (2006.01) |
| *C07C 253/30* | (2006.01) |
| *C07C 253/32* | (2006.01) |
| *C07C 253/34* | (2006.01) |

(52) U.S. Cl.
CPC .......... *C07C 253/30* (2013.01); *B01J 27/228* (2013.01)

(58) Field of Classification Search
CPC ... C07C 255/09; C07C 253/30; C07C 253/34; C07C 253/32; C07C 255/04
See application file for complete search history.

(56) References Cited

U.S. PATENT DOCUMENTS

| | | | |
|---|---|---|---|
| 3,950,370 | A | 4/1976 | Onsager |
| 4,316,857 | A | 2/1982 | Gilbert |
| 4,639,539 | A * | 1/1987 | Hovey .................. C07C 255/00 |
| | | | 558/363 |
| 4,958,042 | A | 9/1990 | Shaw et al. |
| 5,332,844 | A | 7/1994 | Sugise et al. |
| 5,922,901 | A | 7/1999 | Suzuki et al. |
| 5,952,530 | A | 9/1999 | Argyropoulos et al. |
| 6,936,171 | B2 | 8/2005 | Jackson et al. |
| 2008/0083607 | A1 | 4/2008 | Deckert et al. |
| 2014/0364638 | A1 | 12/2014 | Tenn |

FOREIGN PATENT DOCUMENTS

| | | |
|---|---|---|
| CN | 1079463 A | 12/1993 |
| CN | 104010707 A | 8/2014 |
| JP | 5598149 A | 7/1980 |
| JP | 61158953 A | 7/1986 |
| JP | 05-331126 A | 12/1993 |
| JP | 2888392 A | 2/1999 |
| JP | 2002-501938 A | 1/2002 |
| JP | 2015505304 A | 2/2015 |
| KR | 10-1222389 B1 | 1/2013 |
| KR | 10-2014-0108683 A | 9/2014 |
| WO | 93/10082 A1 | 5/1993 |
| WO | 097/01531 A1 | 1/1997 |
| WO | WO-2013095853 A1 * | 6/2013 ......... B01D 11/0426 |

OTHER PUBLICATIONS

Jennings, J.R., and R. J. Cozens, "Catalytic dimerisation of acrylonitrile. I. Homogeneous catalysts from alkyl diarylphosphinites and dialkyl arylphosphonites", Applied Catalysis A: General, 1995, vol. 124, pp. 297-315. (Year: 1995).*
Anderson, Neal G., "Practical Process Research & Development", Elsevier Inc. (2000).

* cited by examiner

*Primary Examiner* — Kamal A Saeed
*Assistant Examiner* — Sagar Patel
(74) *Attorney, Agent, or Firm* — BRYAN CAVE LEIGHTON PAISNER LLP

(57) ABSTRACT

The present disclosure relates to a method for preparing acrylonitrile dimer including: (1) reacting acrylonitrile in the presence of a reaction solvent, a proton-donating solvent, and a phosphorus-based catalyst to prepare an acrylonitrile dimer; and (2) adding an amine-based solvent to a reaction mixture containing the acrylonitrile dimer prepared in (1) and extracting the same to separate the acrylonitrile dimer and the phosphorus-based catalyst.

12 Claims, No Drawings

METHOD OF PREPARING ACRYLONITRILE DIMER

The present application is a National Phase Entry pursuant to 35 U.S.C. § 371 of International Application No. PCT/KR2021/007222 filed on Jun. 9, 2021, and claims priority to and the benefit of Korean Patent Application No. 10-2020-0131026 filed on Oct. 12, 2020 with the Korean Intellectual Property Office, the disclosures of which are incorporated herein by reference in their entirety.

FIELD

The present disclosure relates to a method for preparing acrylonitrile dimer.

BACKGROUND

An acrylonitrile dimer, such as 2-methyleneglutaronitrile (MGN), 1,4-dicyanobutene (DCB) and/or adiponitrile (AND), is a precursor material used in the preparation of a main monomer of nylon 66, a rust inhibitor and a curing accelerator for rubber materials. In addition, it is usefully used in various other fields. As a method of obtaining a dimer of acrylonitrile, dimerizing acrylonitrile in the presence of a phosphorus-based catalyst is commonly used.

However, while the phosphorus-based catalyst used for the reaction has excellent reactivity and selectivity, the reaction proceeds under a homogeneous catalyst system, which would be difficult to separate the catalyst. Distillation is used as a general catalyst recovery method, but due to the high temperature and pressure during distillation, it is likely to cause a decomposition of the catalyst or a side reaction of dimer which is a product.

Thus, in order to effectively extract the catalyst from a homogeneous catalyst system without catalyst decomposition and side reactions, liquid-liquid extraction (LLE) may be used. As an example, U.S. Pat. No. 4,639,539 provides a process of extracting a product with formamide and a catalyst with toluene by using formamide as an extraction solvent and phase separating formamide and toluene which is a reaction solvent. The phase equilibrium system of formamide and toluene has a partition coefficient that is not bad for catalyst separation, but there is a disadvantage in that the product is uniformly dissolved in both of the two solvents and thus, a separation process in each solvent is additionally required to recover the product.

PATENT LITERATURE (Patent Literature 1) U.S. Pat. No. 4,639,539

SUMMARY

In order to solve the above-mentioned problems, the present disclosure provides a method for preparing acrylonitrile dimer which utilizes liquid-liquid extraction (LLE) to block the possibility of decomposition of the catalyst and a side reaction of the product, and uses a solvent that is effective for extraction of only the catalyst.

The present disclosure provides a method for preparing acrylonitrile dimer described below:

A method for preparing acrylonitrile dimer comprising:

(1) reacting acrylonitrile in the presence of a reaction solvent, a proton-donating solvent, and a phosphorus-based catalyst to prepare an acrylonitrile dimer; and (2) adding an amine-based solvent to a reaction mixture containing the acrylonitrile dimer prepared in (1) and extracting the same to separate the acrylonitrile dimer and the phosphorus-based catalyst.

According to the present disclosure, the possibility that a catalyst is decomposed or side reactions proceed in the process of recovering the catalyst can be remarkably reduced, and the catalyst of a single catalyst system can be effectively separated, thereby preparing an acrylonitrile dimer.

DETAILED DESCRIPTION

The present disclosure provides the following preparation method in order to efficiently extract a phosphorus-based catalyst used in the preparation of acrylonitrile dimer:

A method for preparing acrylonitrile dimer comprising the steps of:

(1) reacting acrylonitrile in the presence of a reaction solvent, a proton-donating solvent, and a phosphorus-based catalyst to prepare an acrylonitrile dimer; and (2) adding an amine-based solvent to a reaction mixture containing the acrylonitrile dimer prepared in (1) and extracting the same to separate the acrylonitrile dimer and the phosphorus-based catalyst.

Hereinafter, the present disclosure will be described in detail for each step.

(Step 1: Step of Preparing Acrylonitrile Dimer)

Step 1 of the present disclosure is a step of preparing an acrylonitrile dimer, which is a step of reacting acrylonitrile in the presence of a reaction solvent, a proton-donating solvent, and a phosphorus-based catalyst. Step 1 is not particularly limited as long as it is a conventional method for preparing an acrylonitrile dimer in solution in the presence of a phosphorus-based catalyst. Here, the acrylonitrile dimer includes 2-methyleneglutaronitrile (MGN), 1,4-dicyanobutene (DCB) and/or adiponitrile (AND), and the like.

In one example, the reaction solvent is preferably an inactive reaction organic solvent. The organic solvent inactive to a reaction may include ether solvents such as 1,4-dioxane or diethylene glycol dimethyl ether; amide solvents such as N,N-dimethylacetamide; aromatic hydrocarbon solvents such as toluene, xylene, chlorobenzene, or benzonitrile; aliphatic hydrocarbon solvents such as octane, decane, cyclohexane, or 1,2-dichloroethane, and the like, and toluene, cyclohexane, 1,2-dichloroethane, 1,4-dioxane, chlorobenzene, or xylene is preferred, without being limited thereto. These organic solvents inactive to the reaction may be used either singly or as a mixture of two or more solvents. More preferably, the solvent may be toluene.

The proton-donating solvent is a material that serves to donate protons in the preparation reaction of acrylonitrile dimer, and is not particularly limited as long as it is a proton-donating solvent commonly used in the dimerization reaction of acrylonitrile in the art. In one example, the proton-donating solvent may be water; alcohols such as ethylene glycol, glycerol, methanol, ethanol, isopropanol, isobutanol, propanol, propanediol, butanol, cyclohexanol, or benzyl alcohol; or a mixture thereof, without being limited thereto. Preferably, the proton-donating solvent may be at least one selected from the group consisting of isopropyl alcohol (IPA), butanol, benzyl alcohol, and cyclohexanol, and more preferably, it may be isopropanol (IPA).

The phosphorus-based catalyst may be, preferably, an alkyl diphenyl phosphinite having 1 to 10 carbon atoms. More preferably, the phosphorus-based catalyst may be isopropyl diphenylphosphinite, or ethyl diphenylphosphinite. Here, the alkyl group may be a straight-chain or a branched, and the carbon number is 1 to 10. Specific examples include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylm-ethyl, octyl, n-octyl, tert-octyl, 1-methylheptyl, 2-ethyl-hexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, without being limited thereto.

(Step 2: Step of Separating Acrylonitrile Dimer and Phos-phorus-Based Catalyst)

Step 2 of the present disclosure is a step of separating the acrylonitrile dimer prepared in step 1 and the phosphorus-based catalyst remaining after preparation by liquid-liquid extraction (LLE). In particular, an amine solvent is used as the extraction solvent in order to efficiently extract only the phosphorus-based catalyst from the reaction mixture in which the acrylonitrile dimer, which is a reaction product, and the phosphorus-based catalyst are mixed. The "reaction mixture" is a mixture in which the step of preparing the acrylonitrile dimer of step 1 has been performed, and may include a reaction solvent, a proton-donating solvent, a phosphorus-based catalyst, an acrylonitrile dimer which is a reaction product, and acrylonitrile which is an unreacted material.

The extraction solvent is a solvent used for extracting a target material in liquid-liquid extraction (LLE). The liquid-liquid extraction method is a method of extracting a target material mixed in a liquid sample by a distribution difference using a solvent (extraction solvent) having a higher affinity with the target material than the solvent of a sample. At this time, the liquid sample containing the target material and the extraction solvent must not be mixed with each other, and the extraction solvent is preferably a highly volatile solvent that can be easily removed after extraction. Therefore, in step 2, an amine-based solvent is used as an extraction solvent.

2-methyleneglutaronitrile (MGN), 1,4-dicyanobutene (DCB) and/or adiponitrile (AND), and the like, which are the products of step 1, are not well mixed in the amine-based solvent, and thus are preferable as an extraction solvent. In addition, the partition coefficient of the product of step 1 is higher compared to that of the alkane-based solvent used for extraction of the phosphorus-based catalyst in the general process for preparing acrylonitrile dimer, so that the extrac-tion efficiency is improved, thereby increasing the recovery rate of the phosphorus-based catalyst.

In one example, the partition coefficient ($K_{AM/ADN}$) of the amine-based solvent-adiponitrile of the phosphorus-based catalyst represented by Equation 1 below at 50° C. and 760 torr may be 2.5 or more, 2.6 or more, 2.7 or more, or 2.8 or more. The upper limit of the partition coefficient is not particularly limited, but may be, for example, 6.0 or less, 5.0 or less, or 4.0 or less.

$$K_{AM/ADN} = C_{AM}/C_{ADN} \qquad \text{[Equation 1]}$$

in Equation 1,
$C_{AM}$ is the mass fraction of the phosphorus-based catalyst in the amine-based solvent, and $C_{ADN}$ is the mass fraction of phosphorus-based catalyst in adiponitrile.

Further, the amine-based solvent should have low misci-bility with the acrylonitrile dimer so that only the phospho-rus-based catalyst can be selectively extracted.

The amine-based solvent may preferably have a density of 0.950 g/cm$^3$ or less, or 0.930 g/cm$^3$ or less. Since most of the dimers produced by the dimerization reaction of acryloni-trile are 1,4-dicyanobutene having a density of 1.0 g/cm$_3$ level, acrylonitrile dimer and phase separation may occur smoothly in the extraction step when the $C_{4-10}$ unsaturated hydrocarbon satisfies the above density range.

The amine-based solvent is not particularly limited, but a tertiary amine is preferred. In one example, the amine-based solvent may be at least one selected from the group con-sisting of triethylamine and trioctylamine, and more prefer-ably, triethylamine, trioctylamine or the like may be used. Most preferably, the amine-based solvent may be triethyl-amine.

In step 2, the amount of the amine-based solvent used may be adjusted according to the amount of the reaction mixture to be extracted. In one example, the amine-based solvent may be used in an amount of 80 to 150 parts by weight, or 90 to 130 parts by weight, or 100 to 120 parts by weight, based on 100 parts by weight of the reaction mixture obtained in step 1.

When the amount of the amine-based solvent used is too small, the phosphorus-based catalyst may not be sufficiently extracted and thus, the catalyst component may remain on the acrylonitrile dimer. Conversely, when the amine-based solvent is excessively used, the acrylonitrile dimer may be extracted together, or phase separation from the acrylonitrile dimer may be difficult, and so it is preferable to satisfy the above range.

Preferably, step 2 may be performed at 30° C. or more and 80° C. or less. If the temperature for performing step 2 is less than 30° C., there is a problem that the extraction efficiency of the target material is lowered, and when the temperature exceeds 80° C., there is a problem that the extraction solvent is volatilized.

Preferably, step 2 may be performed for 30 minutes or less. When the extraction is performed for 30 minutes or more, there is a possibility that the process efficiency will decrease. Further, step 2 may be performed for 1 minute or more, 2 minutes or more, or 3 minutes or more.

When the time for performing step 2 is less than 1 minute, the phosphorus-based catalyst may not be sufficiently extracted with the catalyst solvent.

Therefore, the reaction amine-based solvent is sufficiently mixed within the above temperature and time range, and then the mixture is allowed to stand and subjected to phase separation, and an upper layer liquid and a lower layer liquid are separated to complete the extraction.

At this time, the upper layer liquid includes an amine-based solvent and a phosphorus-based catalyst, and the lower layer liquid includes an acrylonitrile dimer.

The upper layer liquid separated with lower layer liquid may be further subjected to a reduced pressure distillation process in order to remove an amine-based solvent and recover a pure phosphorus-based catalyst.

The lower layer liquid, i.e., the acrylonitrile dimer phase, is mostly composed of 1,4-dicyanobutene (DCB), and may contain a small amount of methylene glutaronitrile (MGN). Therefore, in order to remove the MGN, the acrylonitrile dimer phase can be further purified, and subjected to a partial hydrogenation reaction to prepare adiponitrile, which is a precursor of hexamethylenediamine.

The reaction solvent, the proton-donating solvent and unreacted acrylonitrile distilled in step 1, and the phosphorus-based catalyst separated in step 2 may be recovered in a reaction vessel and reused. By recycling the solvent and raw materials of the reaction in this way, the production cost can be reduced and the process efficiency can be enhanced.

Step 2 may further include a step (step 2A) of removing the low boiling point material from the reaction mixture containing the acrylonitrile dimer before the addition of the amine-based solvent. The low boiling point material removed in step 2A may include, for example, a reaction solvent, a proton-donating solvent, and/or an unreacted acrylonitrile. When step 2A is additionally included, the reaction mixture is composed of an acrylonitrile dimer and a phosphorus-based catalyst, so that the extraction efficiency of the phosphorus-based catalyst that is subsequently proceeded can be further increased.

Hereinafter, the present disclosure will be described in more detail by way of examples in order to facilitate the understanding of the invention. However, the examples described below are for illustrative purposes only, and the content of the present disclosure is not limited thereby.

In the Examples and Comparative Examples described below, in order to confirm the extraction efficiency of the extraction solvent, which is an embodiment of the present disclosure, liquid-liquid extraction was performed with an arbitrary reaction mixture containing only the catalyst and the product.

EXAMPLES

Experimental Example 1: Evaluation of Partition Coefficient of Catalyst

To investigate the partition coefficient of the phosphorus-based catalyst to the extraction solvent and acrylonitrile dimer, the following experiment was performed assuming a situation in which the hydrocarbon-based solvent, alcohol, and unreacted acrylonitrile in the reaction mixture were removed through the first purification process.

Isopropyl diphenylphosphinite (0.634 g) as the catalyst and adiponitrile (1.902 g) as the product were mixed to prepare a 25 wt. % solution of isopropyl diphenylphosphinite. To the prepared solution was added 2 ml of triethylamine as an extraction solvent, heated to 50° C., stirred for about 3 to 5 minutes, and then waited until layer separation occurred. When the layers were separated, 0.25 ml of each was extracted from an upper layer liquid (extracted) as the extraction solvent layer and a lower layer liquid (Raffinate) as the adiponitrile layer, and component analysis was performed by GC (GC 2030, Shimadzu). At this time, the detector was FID and was set to 350° C. The column used was HP-5MS and was set at 40~280° C. The temperature of the injection port was 260° C., and the mobile phase used was N₂.

Comparative Experimental Example 1

Layer separation was performed in the same manner as in Experimental Example 1, except that hexane was used as the extraction solvent.

Each of the upper layer liquid and the lower layer liquid extracted in Experimental Example 1 and Comparative Experimental Example 1 was subjected to component analysis by Gas Chromatography (GC), and the fraction of the catalyst contained in each layer was confirmed at 50° C. and 760 torr. Subsequently, the partition coefficient was calculated in accordance with Equation 1 below and shown in Table 1 below.

$$K_{AM/ADN} = C_{AM}/C_{ADN} \qquad \text{[Equation 1]}$$

in Equation 1,
$C_{AM}$ is the mass fraction of the phosphorus-based catalyst in the amine-based solvent, and
$C_{ADN}$ is the mass fraction of phosphorus-based catalyst in adiponitrile.

TABLE 1

| | Extraction solvent | Catalyst mass fraction of upper layer liquid (extracted) $(C_{AM})$ | Catalyst mass fraction of lower layer liquid (Raffinate) $(C_{ADN})$ | Partition co-efficient |
|---|---|---|---|---|
| Experimental Example 1 | tri-ethylamine | 0.2341 | 0.0804 | 2.9117 |
| Comparative Experimental Example 1 | hexane | 0.2033 | 0.0972 | 2.0916 |

As shown in Table 1, the catalyst partition coefficient of Experimental Example 1 using triethylamine was about 1.5 times larger compared to that of Comparative Experimental Example 1 in which commonly used hexane was used as an extraction solvent. That is, it can be confirmed that the phosphorus-based catalyst was better dissolved in triethylamine than in hexane, so that when triethylamine was used as an extraction solvent, the extraction efficiency of the phosphorus-based catalyst was higher.

Example 1

220 ml of toluene, 66 ml of acrylonitrile, and 22 ml of isopropyl alcohol were put into a 1 L reactor, and ethyl diphenylphosphinite (Ph₂POEt) was added in an amount of 3 mol % based on the acrylonitrile. The mixture was stirred and reacted at 60° C. for 3 hours.

After completion of the reaction, the reaction mixture was distilled under a temperature of 80° C. and a pressure of 50 torr, and toluene, isopropanol, and unreacted acrylonitrile were removed from the reaction mixture.

Then, 27 ml of triethylamine was added to the reaction mixture, and then stirred at 50° C. for 5 minutes. After stopping the stirring and allowing to stand so that phase separation occurs, an upper layer liquid and a lower layer liquid were separated, and the components of the upper layer liquid and the lower layer liquid were analyzed using gas chromatography (GC/FID, Shimadzu, FID: 350° C., Column: HP-SMS, 40~280° C., Injection port temperature: 260° C., mobile phase: N₂).

As a result of the analysis, the lower layer liquid was confirmed to contain 79.76 wt. % of 1,4-dicyanobutene (DCB), 3.74 wt. % of methylene glutaronitrile (MGN), 8.186 wt. % of ethyl diphenylphosphinite, and 8.30 wt. % of triethylamine, and the upper layer liquid was confirmed to contain 73.17 wt. % of triethylamine, 24.38 wt. % of ethyl diphenylphosphinite, 2.331 wt. % of 1,4-dicyanobutene (DCB), and 0.109 wt. % of methylene glutaronitrile (MGN).

Comparative Example 1

220 ml of toluene, 66 ml of acrylonitrile, and 22 ml of isopropyl alcohol were put into a 1 L reactor, and ethyl diphenylphosphinite (Ph$_2$POEt) was added in an amount of 3 mol % based on the acrylonitrile. The mixture was stirred and reacted at 60° C. for 3 hours.

After completion of the reaction, the reaction mixture was distilled under a temperature of 80° C. and a pressure of 50 torr, and toluene, isopropanol, and unreacted acrylonitrile were removed from the reaction mixture.

Then, 27 ml of n-hexane was added to the reaction mixture, and then stirred at 50° C. for 5 minutes. After stopping the stirring and allowing to stand so that phase separation occurs, an upper layer liquid and a lower layer liquid were separated, and the components of the upper layer liquid and the lower layer liquid were analyzed using gas chromatography (GC/FID, Shimadzu, FID: 350° C., Column: HP-5MS, 40~280° C., Injection port temperature: 260° C., mobile phase: N$_2$).

As a result of the analysis, the lower layer liquid was confirmed to contain 83.9 wt. % of 1,4-dicyanobutene (DCB), 3.8 wt. % of methylene glutaronitrile (MGN), 9.73 wt. % of ethyl diphenylphosphinite, and 2.48 wt. % of n-hexane, and the upper layer liquid was confirmed to contain 78.71 wt. % of n-hexane, 20.39 wt. % of ethyl diphenylphosphinite, 0.8528 wt. % of 1,4-dicyanobutene (DCB), and 0.039 wt. % of methylene glutaronitrile (MGN).

According to Example 1 and Comparative Example 1, it was confirmed that the catalyst partition coefficient of Example 1 was about 2.98, the catalyst partition coefficient of Comparative Example 1 was about 2.09, and when an amine-based solvent was used as an extraction solvent, the catalyst was better separated in the upper layer liquid.

The invention claimed is:

1. A method for preparing acrylonitrile dimer comprising:
   (1) reacting acrylonitrile in the presence of a reaction solvent, a proton-donating solvent, and a phosphorus-based catalyst to prepare an acrylonitrile dimer;
   (2A) removing the reaction solvent, the proton-donating solvent and unreacted acrylonitrile; and
   (2) adding an amine-based solvent to a reaction mixture containing the acrylonitrile dimer prepared in (1) and extracting the same to separate the acrylonitrile dimer and the phosphorus-based catalyst;

wherein removing the reaction solvent, the proton-donating solvent and unreacted acrylonitrile in (2A) is performed before the addition of the amine-based solvent.

2. The method of claim 1, wherein:
the reaction solvent is at least one selected from the group consisting of toluene, cyclohexane, 1,2-dichloroethane, 1,4-dioxane, chlorobenzene, and xylene.

3. The method of claim 1, wherein
the reaction solvent is toluene.

4. The method of claim 1, wherein
the proton-donating solvent is at least one selected from the group consisting of isopropyl alcohol (IPA), butanol, benzyl alcohol, and cyclohexanol.

5. The method of claim 1, wherein
the proton-donating solvent is isopropyl alcohol (IPA).

6. The method of claim 1, wherein
the phosphorus-based catalyst is an alkyl diphenyl phosphinite having 1 to 10 carbon atoms.

7. The method of claim 1, wherein
the phosphorus-based catalyst is isopropyl diphenylphosphinite, or ethyl diphenylphosphinite.

8. The method of claim 1, wherein the acrylonitrile dimer is an adiponitrile, and
a partition coefficient (K$_{AM/ADN}$) of the amine-based solvent-adiponitrile of the phosphorus-based catalyst represented by Equation 1 at 50° C. and 760 torr is 2.5 or more:

$$K_{AM/ADN} = C_{AM}/C_{ADN} \quad \text{[Equation 1]}$$

in Equation 1,
C$_{AM}$ is the mass fraction of the phosphorus-based catalyst in the amine-based solvent, and
C$_{ADN}$ is the mass fraction of phosphorus-based catalyst in the adiponitrile.

9. The method of claim 1, wherein
the amine-based solvent is at least one selected from the group consisting of triethylamine and trioctylamine.

10. The method of claim 1, wherein
the amine-based solvent is triethylamine or trioctylamine.

11. The method of claim 1, wherein
step (2) is performed at 30° C. or more and 80° C. or less.

12. The method of claim 1, wherein
step (2) is performed for 1 minute or more and 30 minutes or less.

* * * * *